(12) United States Patent
Lee (10) Patent No.: US 11,026,600 B2
(45) Date of Patent: Jun. 8, 2021

(54) ACTIVITY CLASSIFICATION IN A MULTI-AXIS ACTIVITY MONITOR DEVICE

(71) Applicant: InvenSense, Inc., Sunnyvale, CA (US)

(72) Inventor: Jonathan E. Lee, Fremont, CA (US)

(73) Assignee: InvenSense, Inc., San Jose, CA (US)

( * ) Notice: Subject to any disclaimer, the term of this patent is extended or adjusted under 35 U.S.C. 154(b) by 951 days.

(21) Appl. No.: 13/648,963

(22) Filed: Oct. 10, 2012

(65) Prior Publication Data

US 2013/0179110 A1    Jul. 11, 2013

Related U.S. Application Data

(60) Provisional application No. 61/584,710, filed on Jan. 9, 2012.

(51) Int. Cl.
*A61B 5/11* (2006.01)
*G01R 33/028* (2006.01)
*A61B 5/00* (2006.01)

(52) U.S. Cl.
CPC ........... *A61B 5/1118* (2013.01); *A61B 5/1123* (2013.01); *G01R 33/028* (2013.01); *A61B 5/0002* (2013.01); *A61B 5/1116* (2013.01)

(58) Field of Classification Search
CPC ... A61B 5/1118; A61B 5/1123; A61B 5/1116; A61B 5/0002; G01R 33/028
See application file for complete search history.

(56) References Cited

U.S. PATENT DOCUMENTS 7,634,379 B2 * 12/2009 Noble ........................... 702/141
7,715,982 B2 *  5/2010 Grenfell et al. ............... 701/468
2003/0226695 A1    12/2003 Mault
2005/0108660 A1 *  5/2005 Cheng et al. .................. 715/863
2007/0293374 A1    12/2007 Chan
2008/0018532 A1 *  1/2008 Mackintosh et al. ..... 342/357.12
(Continued)

FOREIGN PATENT DOCUMENTS

AU    WO 2010083562 A1 *  7/2010 ........... A61B 5/1123
CA            2563139 A1 *  5/2007
(Continued)

OTHER PUBLICATIONS

Ghasemzadeh, H., Loseu, V., Guenterberg, E., and Jafari, R., "Sport Training Using Body Sensor Networks: A Statistical Approach to Measure Wrist Rotation for Golf Swing", 2009, Published by BodyNets, p. 2.*

(Continued)

*Primary Examiner* — Alexander Satanovsky
*Assistant Examiner* — John Kuan
(74) *Attorney, Agent, or Firm* — Bay Area Technology Law Group PC (57) ABSTRACT

An activity classification device is disclosed. The activity classification device comprises one or more motion sensors and a memory configured to receive signals from the one or more motion sensors. The device further includes a processor in communication with the memory. Finally, the device includes a classification algorithm executed by the processor, the classification algorithm for identifying activities that a user is engaged in. The memory may also record a user's activity log, calorie count and an RF module, which transmits the recorded data to a host either upon request or continuously.

17 Claims, 6 Drawing Sheets

(56) References Cited

U.S. PATENT DOCUMENTS

| | | |
|---|---|---|
| 2008/0171922 A1 | 7/2008 | Teller et al. |
| 2009/0233770 A1 | 9/2009 | Vincent et al. |
| 2010/0009650 A1 | 1/2010 | Orr et al. |
| 2010/0056872 A1* | 3/2010 | Kahn .................. A61B 5/1038 600/300 |
| 2010/0079291 A1 | 4/2010 | Kroll et al. |
| 2010/0214216 A1* | 8/2010 | Nasiri et al. .................. 345/158 |

FOREIGN PATENT DOCUMENTS

| | | |
|---|---|---|
| CN | 101458739 | 6/2009 |
| CN | 101520815 | 9/2009 |
| CN | 102265242 | 11/2011 |
| WO | WO03/001340 | 1/2003 |

OTHER PUBLICATIONS

Huynh et al., "Analyzing Features for Activity Recognition" Joint sOc-EUSAI conference, Grenoble, Oct. 2005.*

Ling Bao and Stephen S. Intille, "Activity Recognition from User-Annotated Acceleration Data," Pervasive 2004, LNCS 3001, pp. 1-17, 2004.

* cited by examiner

ACTIVITY CLASSIFICATION IN A MULTI-AXIS ACTIVITY MONITOR DEVICE

CROSS-REFERENCE TO RELATED APPLICATION

This application claims the benefit under 35 USC 119(e) of U.S. Provisional Patent Application No. 61/584,710, filed on Jan. 9, 2012, entitled "ACTIVITY CLASSIFICATION IN A MULTI-AXIS ACTIVITY MONITOR DEVICE," which is incorporated herein by reference in its entirety.

FIELD OF THE INVENTION

The present invention relates generally to monitoring devices using sensors and more specifically to classifying activities utilizing such devices.

BACKGROUND OF THE INVENTION

Devices for providing inertial activity classification are utilized in a variety of environments. These devices can comprise of accelerometers. Typically the devices record or transmit data that are used for classifying activity based on features derived from accelerometer to a host device for processing.

However, it is important for power consumption to be limited in portable device applications such as laptops, tablets, smartphones and the like. Therefore what is desired is a system and method to provide an activity classification in a monitoring device that is accurate, low power, and cost effective. The present invention addresses such a need.

SUMMARY OF THE INVENTION

The present invention discloses a device. The device comprises one or more motion sensors and a memory configured to receive signals from the one or more motion sensors. The device further includes a processor in communication with the memory. Finally, the device includes a classification algorithm executed by the processor, the classification algorithm for identifying activities. The device also may include a memory unit to record data such as activity log and calorie count among other data. In an embodiment, the sensor may include (Radio Frequency) RF module to wirelessly transmit the recorded data to the host either upon request or continuously.

DETAILED DESCRIPTION

The present invention relates generally to monitoring devices and more specifically to classifying activities utilizing such devices. The following description is presented to enable one of ordinary skill in the art to make and use the invention and is provided in the context of a patent application and its requirements. Various modifications to the preferred embodiments and the generic principles and features described herein will be readily apparent to those skilled in the art. Thus, the present invention is not intended to be limited to the embodiments shown, but is to be accorded the widest scope consistent with the principles and features described herein.

A system and method in accordance with the present invention describes an inertial activity classification device, comprising of any combination of sensors, such as an accelerometer, gyroscope, temperature sensor, pressure sensor, magnetometer, or microphone, and a method for classifying an activity based on features derived from inertial data, and the ability to continually report an activity derived from physical activity.

In an embodiment the system and method improves the long-term viability of a multi-sensor inertial activity classification device by offering a decision scheme for power management, allowing the usage of relatively higher power devices, such as a gyroscope, for more accurate sensing and activity classification without the associated reduction in battery life.

A system and method in accordance with an embodiment also provides an improvement in the accuracy of a device by being able to identify walking, jogging, and running phases of motion, for the purpose of increasing the relevance of the reported data for calorie counting purposes, and also to reject false positive "steps" in the counted number of steps. The identification of activities allows the device to more accurately track steps when walking, running, etc., while rejecting "steps" recorded during shaking, driving, or other inactive movements. Accordingly motion tracking information, such as number of steps to be reported at an appropriate time is allowed based on an activity.

To describe the features of the present invention in more detail refer now to the following description in conjunction with the accompanying Figures.

Figure 1:
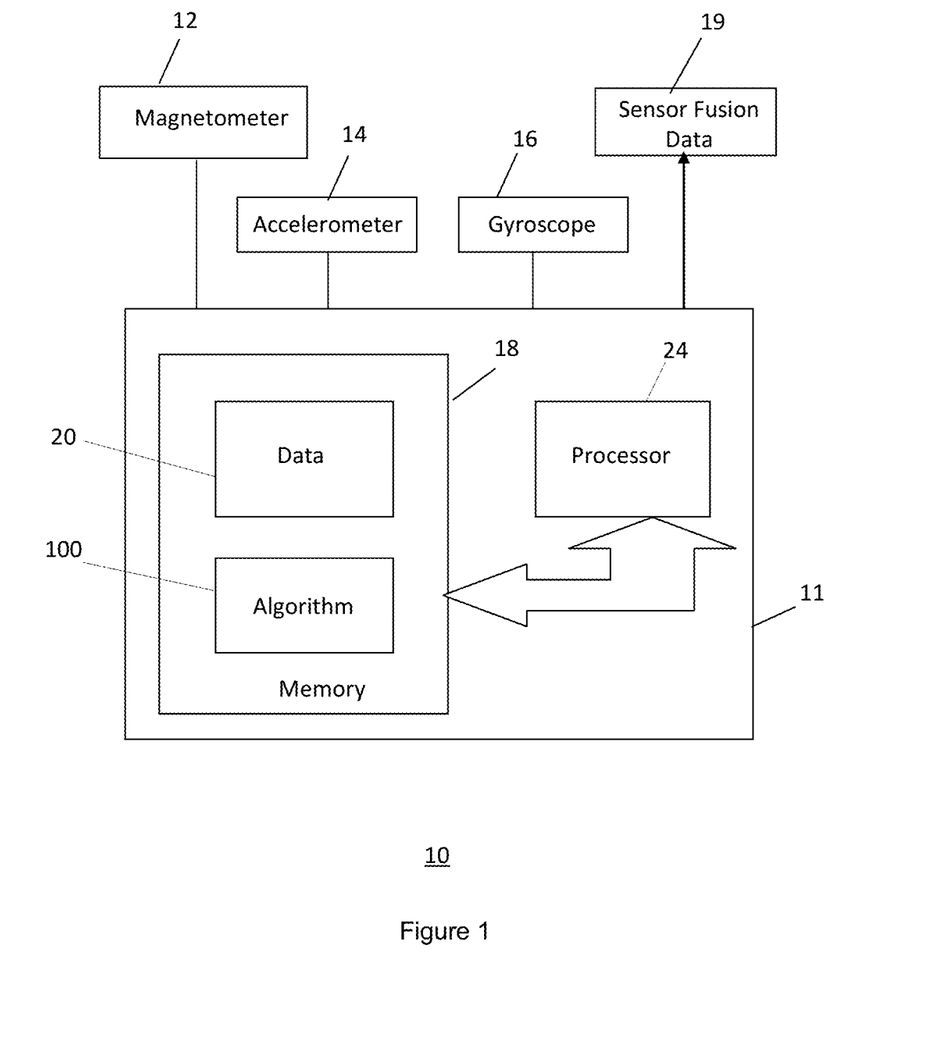
FIG. 1 is a block diagram of a system that utilizes an activity classification algorithm in accordance with an embodiment.

FIG. 1 is a block diagram of a system 10 that utilizes an activity classification algorithm 100 in accordance with an embodiment. The system 10 includes a device 11. The device 11 may include any type of mobile device including but not limited to, a cell phone, a tablet PC, or other type of portable electronic device. The device 11 receives input data from a plurality of sensors such as one or more magnetometers 12, one or more accelerometers 14 and one or more gyroscopes 16. Although the sensors 12, 14 and 16 are shown external to the device 11, one of ordinary skill in the art readily recognizes that those sensors could be internal to the device 11 and that would be within the spirit and scope of the present invention.

The device 11 includes memory 18 for storing data. In the described embodiment, sensors refer to magnetometer 12, accelerometer 14 or gyroscope 16. Data 20 stores data from the one or more sensors. Memory 18 also includes algorithm 100 in accordance with the present invention. Algorithm 100 may include software code for, but not limited to activity classification and sensor fusion. In the described embodiments, sensor fusion may include consolidating data from magnetometer 12, accelerometer 14 and gyroscope 16 and generating sensor fusion data. A processor 24 executes the algorithm 100 which operates on the data received from the sensors. The processor 24 provides the sensor fusion data 19. The sensor fusion data 19 provides orientation information of the device.

A system that utilizes an activity classification algorithm 100 in accordance with the present invention can take the form of an entirely hardware implementation, an entirely software implementation, or an implementation containing both hardware and software elements. In one implementation, this activity classification algorithm is implemented in software, which includes, but is not limited to, application software, firmware, resident software, microcode, etc.

Furthermore, the activity classification algorithm 100 can take the form of a computer program product accessible from a computer-usable or computer-readable medium providing program code for use by or in connection with a computer or any instruction execution system. For the purposes of this description, a computer-usable or computer-readable medium can be any apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk, and an optical disk. Current examples of optical disks include DVD, compact disk-read-only memory (CD-ROM), and compact disk-read/write (CD-R/W). To describe the features of the present invention in more detail, refer now to the following description in conjunction with the accompanying Figures.

In an embodiment an inertial activity classification device includes any combination of sensors, such as an accelerometer, gyroscope, temperature sensor, pressure sensor, magnetometer, or microphone, and an algorithm for classifying an activity based on features derived from inertial data, and the ability to continually report an activity derived from physical activity. A system in accordance with an embodiment relies on multiple sensors and an activity classification algorithm in order to improve accuracy of the activity recognition results. The inclusion of a sensor has the effect of improving accuracy, stability, or algorithm performance.

Figure 2A:
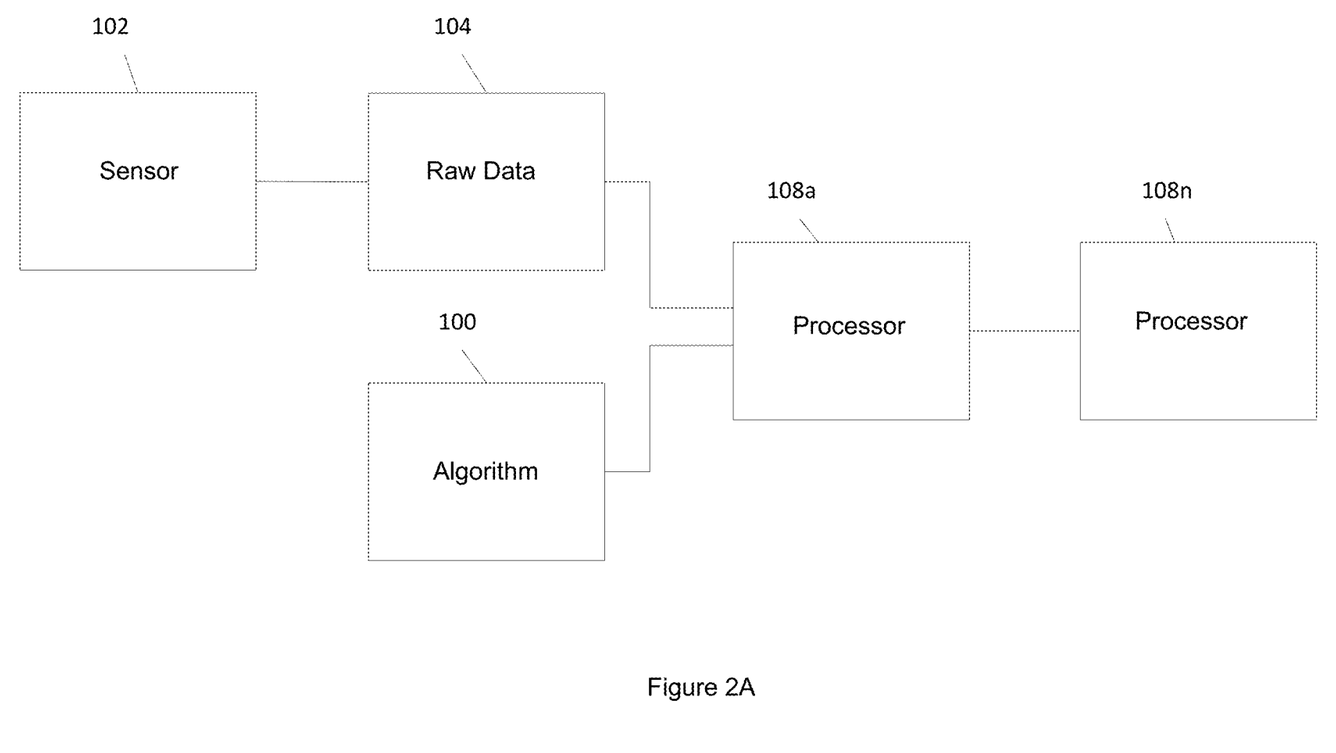
FIG. 2A is a diagram of an activity classification system wherein more than one processor is operating in accordance with an embodiment.

FIG. 2A is a diagram of an activity classification system 100 wherein more than one processor is operating in accordance with an embodiment. In an embodiment, components include one or more sensors 102, raw data 104, the activity classification algorithm 100, and one or more processors 108a-108n. The set of sensors could be any combination of a 1, 2, or 3-axis accelerometer, a 1, 2, or 3-axis gyroscope, a 1, 2, or 3-axis magnetometer, a pressure sensor, a temperature sensor, and a microphone.

Figure 2B:
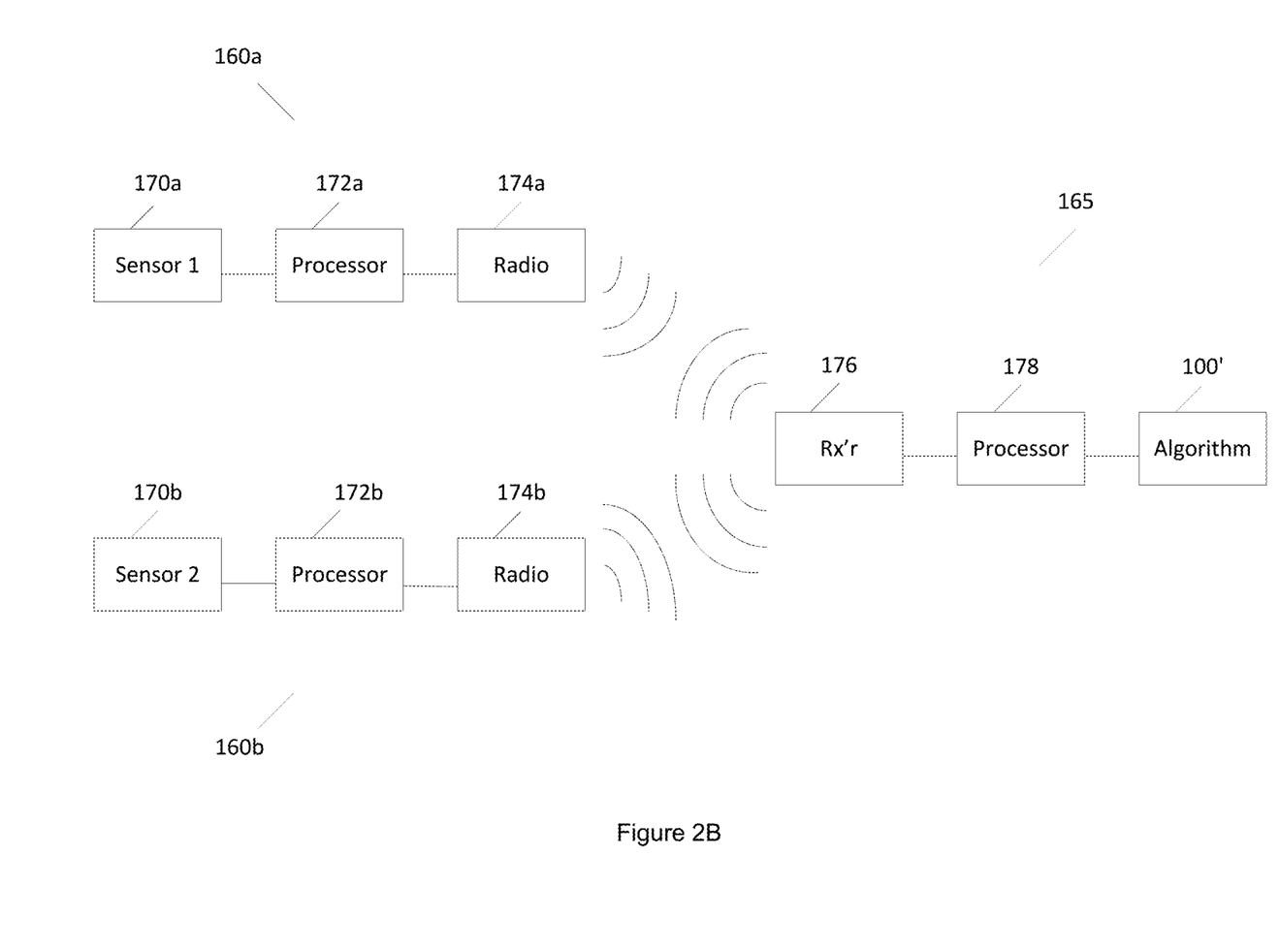
FIG. 2B is a diagram of an activity classification system wherein more than one sensor is utilized in a wireless environment in accordance with an embodiment.

Such an activity could also be utilized in an embodiment where there are one or more sensors worn by a user on various parts of the body. FIG. 2B is a diagram of an activity system 150 wherein one or more sensors are utilized in a wireless environment in accordance with an embodiment.

As is seen, the activity stem includes two sensor systems 160a and 160b that communicate wirelessly to a host system 165. Host system 165 can be connected wirelessly to any number of sensor systems. In an example, sensor system 160a could be attached to an arm of a user and sensor system 160b could be could be coupled to a leg of the user. Each of the sensor systems 160a and 160b include a sensor 170a and 170b respectively for receiving activity data. Each of the sensors 170a and 170b is coupled to a processor 172a and 172b respectively which receives the activity data from the sensor. Each of the processors 172a and 172b then provides the data to its respective radio 174a and 174b. The radios 174a and 174b transmit the data wirelessly to the host system 165. The host system 165 comprises a wireless receiver 176 which receives the data from radios 174a and 174b and a processor 178 which executes the activity classification algorithm 100'.

In another embodiment, sensor systems and the host system can be connected by wires. In another embodiment, the host system can reside on a sensor system and connect to other sensor systems.

Figure 3:
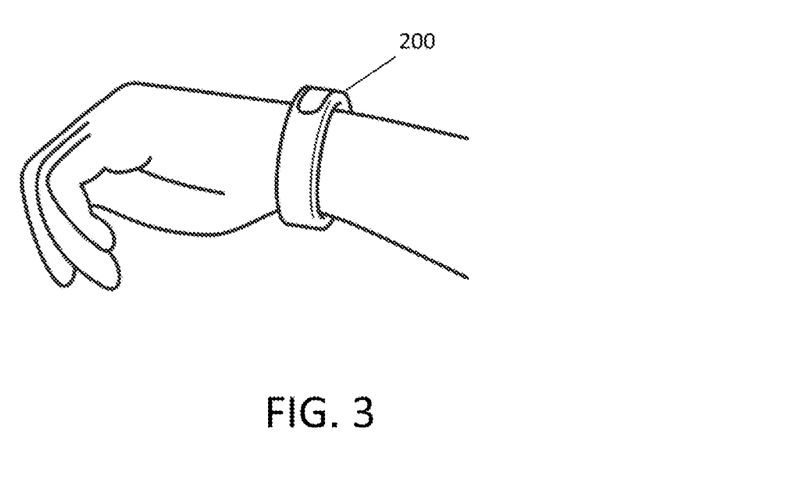
FIG. 3 illustrates an embodiment of an activity classification device to be worn as if it were a wrist watch.

FIG. 3 illustrates an activity classification device 200 to be worn as if it were a wrist watch. Activity classification device 200 is strapped to a user and is designed for portable media devices. In operation, a wearable module's microcontroller within the device 200 collects data from the inertial sensors, such as a gyroscope and or accelerometer within the device 200, calculating a set of features from each data. In an implementation, included are a signal mean, standard deviation, energy, and entropy, as calculated from signal sources; raw accelerometer magnitude, raw gyroscope magnitude, and calculated signals resulting from a set of libraries that provide data for motion processing, such as: linear world-frame acceleration (X, Y, Z), linear body-frame acceleration (X, Y, Z), angular world frame rate (X, Y, Z), angular body frame rate (X, Y, Z), utilizing the following calculators.

$$\text{Accelerometer/Gyro Magnitude} = \sqrt{X^2 + Y^2 + Z^2} \qquad \text{Equation 1}$$

Mean and standard deviation are simple measures of the average value, and typical variance of the source signal. Energy and Entropy are the result of measures of a frequency space transformation, using an FFT. Energy is a measure of the "energy" of a signal which results from frequency information (i.e. steady state or DC signals have energy of 0), while Entropy (also called "spectral entropy") is a measure of how spread apart the signal frequencies are (lower value indicate fewer frequencies, while higher values indicate multiple frequencies present in the source signal. For example, these features can be calculated over a 10 second data collection period (approximately 1024 data points @ 100 Hz data collection rate), using the following equations:

$$\text{Mean} = \sum_{i=1}^{n} \frac{X(i)}{n} \qquad \text{Equation 2}$$

$$\text{Standard Deviation} = \sqrt{\sum_{i=1}^{n}(X(i) - X_{\text{mean}})^2 / (n-1)} \qquad \text{Equation 3}$$

$$\text{Energy} = \sum_{i=1}^{n} FFT_x(i)^2 / n \qquad \text{Equation 4}$$

$$\text{Entropy} = \sum_{i=1}^{n}(FFT_x(i))(\log(FFT_x(i))/n \qquad \text{Equation 5}$$

Where n=number of samples within the collection period, and FFTx contains the elements of a Fast Fourier Transform of the original signal.

Referring back to FIG. 2, in an embodiment, signal features calculated within the device, or raw data 104 can be transmitted to a host device 108a-108n or other microcontroller based system, where the features can be calculated in real time. The processing power required is largely dominated by the ability to take an FFT of the signal. While not required for the present invention, the inclusion of the FFT based features improve the accuracy of the system and improve the performance of the pedometer feature.

Additional features may be added, based on the FFT results, or other transformations, i.e. Wavelet Transforms (used commonly in image compression technology), run length-encoding, differentiation, integration, or a combination of those techniques.

Using the features, activities can be differentiated from one another for analyzing whether the user is wearing the device (or not), and detecting what activity the user is engaged in. For example, when the activity transitions between standing, to walking, to running, the values of features increase, and a simple rule can be created for a feature. If an accelerometer standard deviation is above some threshold A, then the user is assumed to be running; otherwise, if the accelerometer standard deviation is above threshold B, the user is assumed to be walking, else the user is assumed to be standing, and therefore no "steps" should be recorded, as they likely occur from another type of activity. With a collection of independent features for every 10 seconds of data collected, numerous rules can be created which identify an activity into one of those categories.

Figure 4:
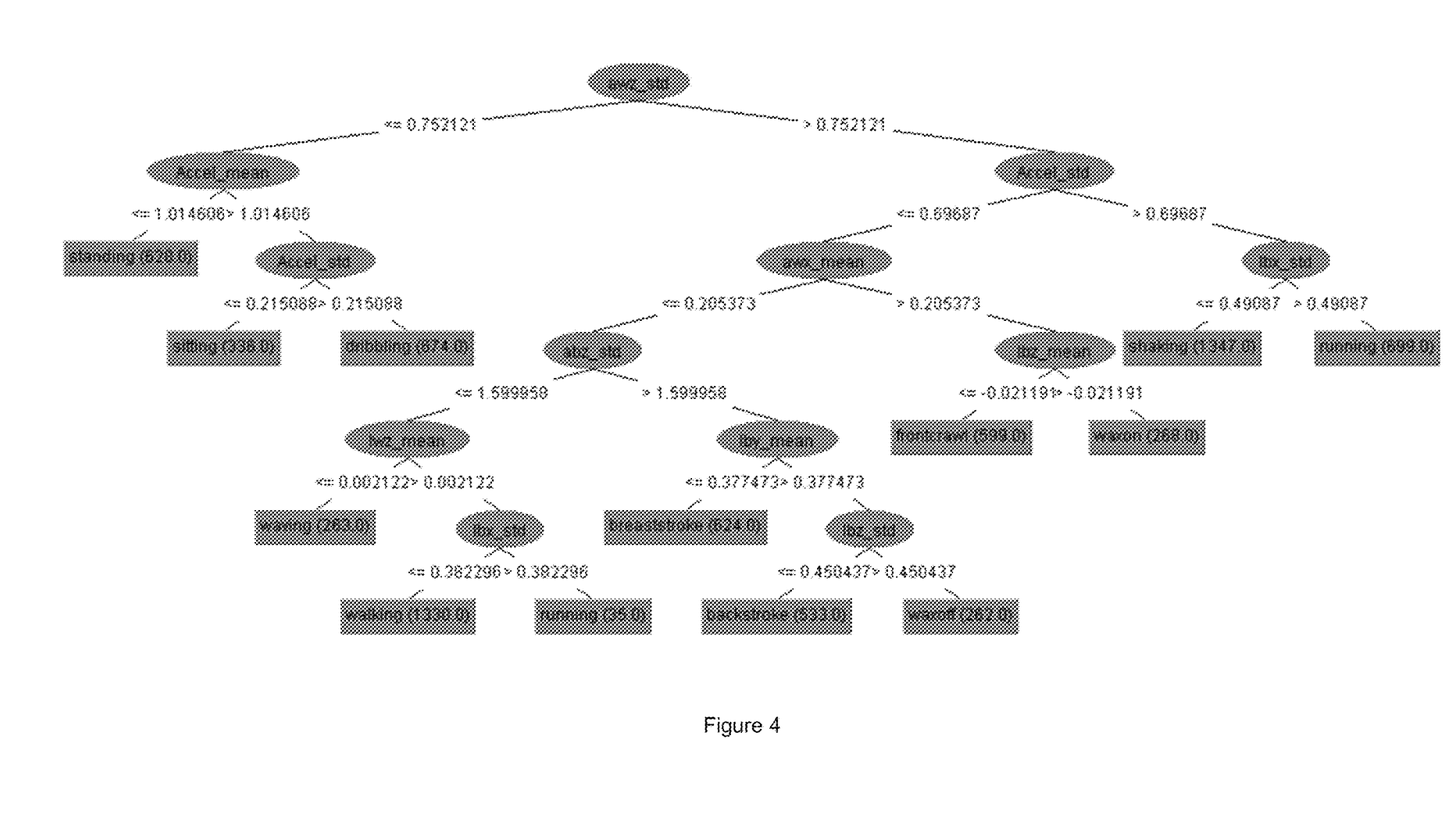
FIG. 4 illustrates an example of an algorithm for a decision tree generation that is utilized to identify a plurality of activities.

FIG. 4 illustrates an example of an algorithm for a decision tree 400 generation that is utilized to identify a plurality of activities. To improve the performance and accuracy of the approach, modern machine learning and statistical processing techniques can be applied. For example, the algorithm can be applied to previously classified sets of data collected during "walking," "running," "stair climbing," or a number of other activities that would not be associated with a step, such as "waving," "shaking," "sitting," "driving a car," etc. There are published algorithms such as C4.5 which uses a technique of choosing features to classify the data based on maximizing the information entropy gained by using a specific feature.

Using the C4.5, a decision tree 400 can be generated to classify the current sensed features, calculated from the inertial sensor values, with a high degree of accuracy (typically above 95%). The decision tree 400 may be calculated on the device itself, or as a post or pre-process in which the decision tree 400 is classified based on previously collected data, then programmed or "hard coded" into the device itself. Ideally a user will have been "trained" into the classifier set, to maximize the performance and accuracy of user activity classification, although with a sufficient sample of similar users, "training" is not required. Including a multitude of users within a training set creates a generalized classifier, which improves performance of un-trained users.

Alternate algorithms exist (ID3, See5, K-means clustering, HMM's, etc.) which could be applied instead of the C4.5 technique to generate the decision tree. Clustering techniques involve computing the likelihood a current set of features matches a specific activity by comparing the relative "distance" between the feature groups. Such techniques have been successfully applied and tested in accordance with an embodiment.

In an embodiment the system and method improves the long-term viability of a multi-sensor inertial activity classification device by offering a decision scheme for power management, allowing the usage of relatively higher power devices, such as a gyroscope, for more accurate sensing and activity classification without the associated reduction in battery life.

Figure 5:
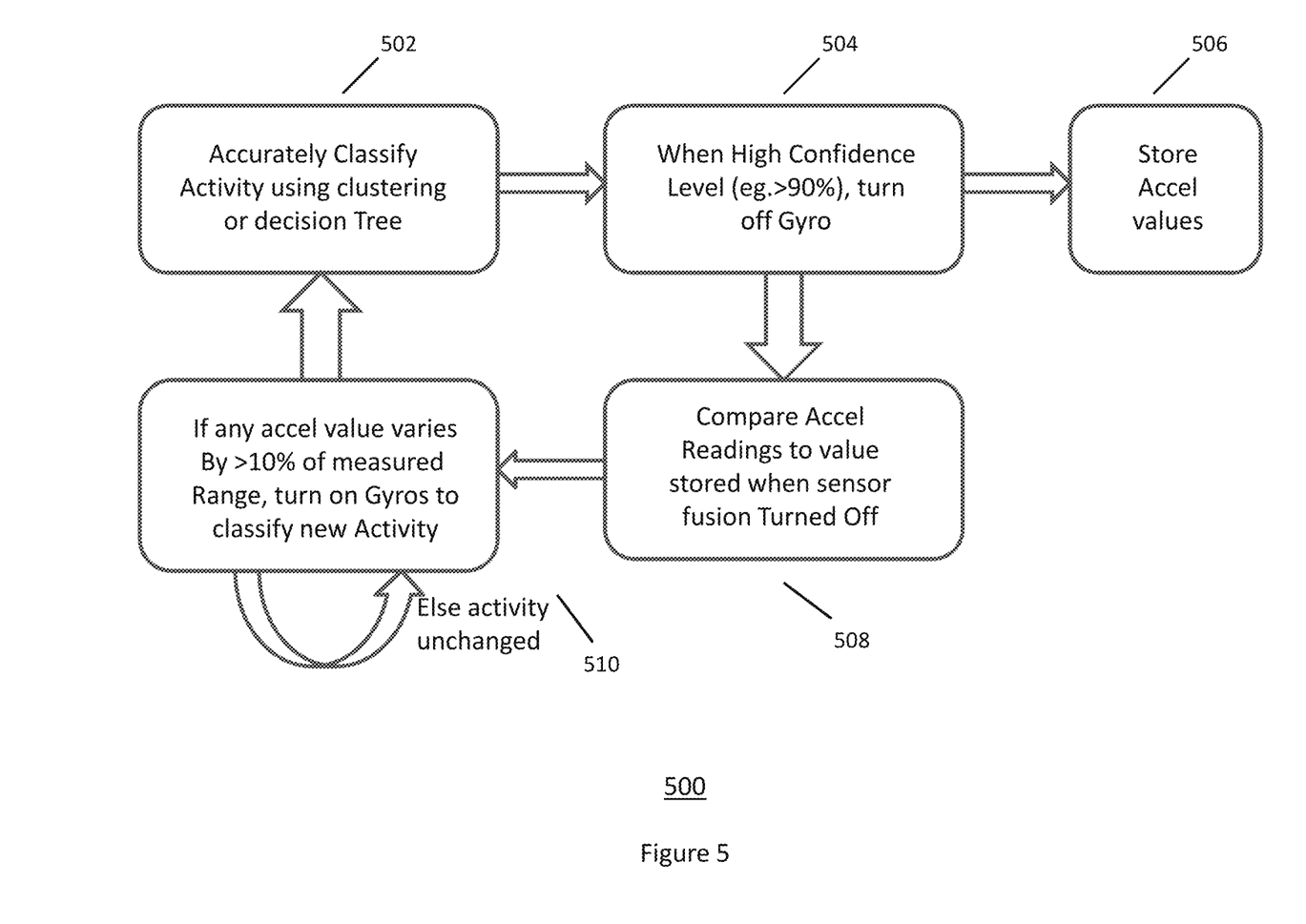
FIG. 5 illustrates the power management process for accelerometer variance tracking in accordance with an embodiment.

FIG. 5 illustrates the power management process 500 for low power mode sensor variance tracking in accordance with an embodiment. In an embodiment, the power management process 500 resides within the activity classification algorithm. The power management process 500 utilizes the set of sensors and their derived features that can be utilized to correctly classify activities with a high degree of accuracy. The power management process 500 can then be put in a low power mode until the low power mode sensors measure an activity transition. In the described embodiments, a low power mode refers to reducing the sampling data rate of sensors or placing the device in standby or shutting off one or more sensors that are being fed into the algorithm. Typically, low power is accomplished by placing the gyroscope in a standby mode.

Sensor output magnitude, linear world frame acceleration, linear body acceleration, angular world frame rate, and angular body frame rate, are used for the activity classification step.

Referring back to FIG. 5, first the activity classification device operates in "Full Power Mode" where a gyroscope, an accelerometer, and a magnetometer (if present) collect data, and a microcontroller processes all relevant features. The device then performs activity classification based on clustering, decision tree, or other some other model with confidence, via step 502 where the activity is recognized.

Second, when the confidence level of the reported activity is sufficiently high, the device can store the current accelerometer values in 506 and then shut off the gyroscope, v, to enter a "Low Power Mode." Confidence may be computed, via step 502 as the percentage of feature sets/samples identified as the current activity during a predetermined time period such as the last 10 seconds, or by distance from the current sample to the appropriate generated cluster, or other method.

Third, when in "Low Power Mode" the accelerometer is still active and collecting data. The values and associated features stored in step 506 are compared as to whether transitioning to a new activity, by comparing the variance between the current data and stored values when sensor fusion is turned off, via step 508.

Fourth, the value of the variance of accelerometer derived features is evaluated. If the variance is sufficiently large, the device will transition back to "full power mode", to classify the current (assumed to be different) activity, via step 510. It is possible, and perhaps desirable, to also trigger the reclassification if the activity transitions to sub-activities (slower running/jogging as compared to sprint running), so levels can be chosen which allow for the activity transitions while maintaining a reasonable range of values where the sensor will remain off, thus saving power.

The power management process is the equivalent of storing the low power mode features of an activity e.g. "running," detecting a change in the low power mode features which would indicate a new activity. By comparing each feature independently, the likelihood of detecting a new trained activity with the power management process is high.

By utilizing the power management process, the device will save power according to the amount of time a specific activity is maintained. "Sitting," "Sleeping," "Standing," "Driving," or "Walking" can be assumed to last for several hours throughout the day, while short periods of heavy activity, such as: "Making dinner" or "Getting into the car" would be expected to require the gyroscope to be "on" for correct identification, but would last for much shorter amounts of time.

When the activity classification process is applied to a device, it allows a device carried by the user (attached to wrist, foot, hip, chest, etc., through various attachment techniques) to track different phases of activity, from stopped/standing to a slow walk, fast walk, jog, run, sprint, etc. and report them via an on-screen display or other indicator, as well as report analytically the calories burned for each of those activities.

Once the activity has successfully been classified, an application may run on the data, analyzing the step frequency and event. In an embodiment, the application may choose to increment a step counter when a user is classified as "walking" or "running," but may reject a user standing and shaking the pedometer up and down, or a device jostling loosely in the back of a vehicle, for example.

The application of machine learning and activity classification allows an activity classification device to utilize a set of sensors, including accelerometers, gyroscopes, magnetometers, pressure sensors, temperature sensors, microphones, etc. by implementing a power management methodology based on the measured feature-space variance of any sensor, or combination of sensors. With the activity classification device, a lower power sensor (or combination of sensors) can be used to detected transitions between activities, while a larger set of sensors may be used for a short period of time to classify the activity.

The application of machine learning and activity classification allow a typical digital pedometer to increase its level of accuracy and improve functionality, particularly for long-term data collection. An implementation in accordance with an embodiment requires certain training steps to be performed with the device, in recognizing the user (or a representative set of users) to analyze walking, running, standing, etc. For best results, a training step should be included to allow the end user to "classify" their own activities, so that their specific motion features might be correctly identified.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the present invention.

What is claimed is:

1. A device comprising:
   motion sensors including a gyroscope and an accelerometer;
   a memory configured to receive signals from the motion sensors;
   a processor in communication with the memory;
   a classification algorithm executed by the processor; the classification algorithm for identifying activities that a user is engaged in using the gyroscope and the accelerometer and for assigning a confidence value to an identified activity; and
   a power management algorithm that (i) stores data from the accelerometer associated with the identified activity and disables the gyroscope when the confidence value exceeds a threshold and (ii) compares subsequent data from the accelerometer to the stored data and enables the gyroscope when variance between the subsequent data and the stored data is sufficiently large.

2. The device of claim 1, wherein the motion sensors comprise any or any combination of one or more accelerometers, one or more gyroscopes, one or more magnetometers, one or more pressure sensors, one or more temperature sensors, one or more microphones, and one or more heart rate monitors.

3. The device of claim 1, wherein each of the motion sensors is an integrated module on a single substrate.

4. The device of claim 1, further comprising a step counter based on any combination of the identified activity or identified activity transitions, and reporting a number of steps.

5. The device of claim 1, wherein the memory is configured to store an activity data.

6. The device of claim 5, further comprising a circuit which wirelessly transmits the activity data to a second device.

7. The device of claim 1, wherein the classification algorithm includes estimating a calorie burn rate based on the identified activities.

8. The device of claim 1, wherein the identified activities include any of sleeping, driving a car, bicycling, jogging, playing tennis, golfing, sitting, standing, walking, running, swim strokes, waving motions and moving hand in circles.

9. The device of claim 8, wherein the swim strokes comprise any of a breaststroke, a backstroke, and freestyle and the waving motions include any of a handshake, dribbling.

10. A computer-implemented method for identifying activities of a device, the method comprising:
    utilizing motion sensors on the device including a gyroscope and an accelerometer to identify activities;
    utilizing a classification algorithm executed by a processor; the classification algorithm for identifying the activities and for assigning a confidence value to an identified activity; and
    utilizing a power management algorithm executed by the processor that (i) stores data from the accelerometer associated with the identified activity and disables the gyroscope when the confidence value exceeds a threshold and (ii) compares subsequent data from the accelerometer to the stored data and enables the gyroscope when variance between the subsequent data and the stored data is sufficiently large.

11. The computer-implemented method of claim 10, wherein the utilizing motion sensors comprises executing a classification algorithm to identify activities.

12. The computer implemented method of claim 11, which includes estimating a calorie burn rate based on the identified activities by the classification algorithm.

13. The computer-implemented method of claim 10, wherein the identified activities include any of sitting, standing, walking, running, swim strokes, waving motions and moving hand in circles.

14. The computer-implemented method of claim 13, wherein the swim strokes comprise any of a breaststroke, a backstroke, and freestyle and the waving motions include any of a handshake, dribbling.

15. A computer program product containing program instructions for identifying activities of a device on a non-transitory computer-readable medium, the program instructions to be executed by a processor, the program instructions when executed comprising:
    utilizing motion sensors on the device including a gyroscope and an accelerometer to identify activities of the device;
    utilizing a classification algorithm executed by the processor; the classification algorithm for identifying the activities and for assigning a confidence value to an identified activity; and
    utilizing a power management algorithm executed by the processor that (i) stores data from the accelerometer associated with the identified activity and disables the gyroscope when the confidence value exceeds a threshold and (ii) compares subsequent data from the accelerometer to the stored data and enables the gyroscope when variance between the subsequent data and the stored data is sufficiently large.

16. The computer program product of claim 15, further comprising repeating the utilizing motion sensors step to improve confidence level, accuracy, and performance of the device.

17. A system comprising:
   at least one host device comprising a first processor;
   a first memory;
   a first wireless communication module; and
   a classification algorithm executed by the first processor; the classification algorithm for identifying activities that a user is engaged in and for assigning a confidence value to an identified activity; and
   at least one sensor device, each of the sensor devices comprising one or more motion sensors selected from a gyroscope and a gyroscope, such that the system comprises at least one gyroscope and at least one accelerometer; a second memory configured to receive signals from the one or more motion sensors; a second processor in communication with the second memory; and a second wireless communication module to communicate with the at least one host device via the first wireless communication module, wherein the second processor executes a power management algorithm to (i) store data from the accelerometer associated with the identified activity and disable the gyroscope when the confidence value exceeds a threshold and (ii) compare subsequent data from the accelerometer to the stored data and enable the gyroscope when variance between the subsequent data and the stored data is sufficiently large.

* * * * *